United States Patent
Kim (10) Patent No.: US 12,009,108 B2
(45) Date of Patent: Jun. 11, 2024

(54) DENTAL FORMULA INFORMATION INPUT METHOD, DENTAL FORMULA INFORMATION INPUT DEVICE, AND RECORDING MEDIUM

(71) Applicant: Osstemimplant Co., Ltd., Seoul (KR)

(72) Inventor: Si Hyung Kim, Incheon (KR)

(73) Assignee: Osstemimplant Co., Ltd., Seoul (KR)

( * ) Notice: Subject to any disclaimer, the term of this patent is extended or adjusted under 35 U.S.C. 154(b) by 130 days.

(21) Appl. No.: 17/432,162

(22) PCT Filed: Feb. 14, 2020

(86) PCT No.: PCT/KR2020/002118
§ 371 (c)(1),
(2) Date: Aug. 19, 2021

(87) PCT Pub. No.: WO2020/171484
PCT Pub. Date: Aug. 27, 2020

(65) Prior Publication Data
US 2022/0254511 A1    Aug. 11, 2022

(30) Foreign Application Priority Data
Feb. 20, 2019 (KR) .................. 10-2019-0019761

(51) Int. Cl.
*G16H 70/20* (2018.01)
*A61C 13/08* (2006.01)

(52) U.S. Cl.
CPC ........... *G16H 70/20* (2018.01); *A61C 13/082* (2013.01); *A61C 2201/002* (2013.01)

(58) Field of Classification Search
CPC ........ G16H 70/00; G16H 70/20; G16H 20/00; G16H 40/63; G16H 10/60; A61C 13/00;
(Continued)

(56) References Cited

U.S. PATENT DOCUMENTS 9,662,188 B2 * 5/2017 Laubersheimer .. A61C 13/0004
2008/0090197 A1 * 4/2008 Touchstone ............ A61C 19/10
433/26
(Continued)

FOREIGN PATENT DOCUMENTS

JP    2014147482 A    8/2014
KR    10-1137023 B1    4/2012
(Continued)

OTHER PUBLICATIONS

C. L. Rizzatti, M. Rudek, A. L. Szejka, O. Canciglieri and M. Trajanovic, "Proposal for an image-based software system for dental implant positioning," 2015 IEEE 15th International Conference on Bioinformatics and Bioengineering (BIBE), Belgrade, Serbia, 2015, pp. 1-6, doi: 10.1109/BIBE.2015.7367726. (Year: 2015).*

(Continued)

*Primary Examiner* — Evangeline Barr
*Assistant Examiner* — Patricia K. Edouard
(74) *Attorney, Agent, or Firm* — Downs Rachlin Martin PLLC (57) ABSTRACT

A dental formula information input method and a dental formula information input device for automatically inputting dental formula information about teeth are disclosed. The dental formula information input method creates a library from dental formula information about teeth universally used for prosthetic work, and then automatically inputs the dental formula information about teeth through one click on the basis of the library, thereby minimizing work steps and enabling an increase in the convenience and usability of a user inputting cases relating to prosthetic work.

9 Claims, 7 Drawing Sheets

(58) Field of Classification Search
CPC .............. A61C 13/0004; A61C 13/082; A61C 2202/002; A61B 6/14; A61B 6/5211; G05B 19/409
See application file for complete search history.

(56) References Cited

U.S. PATENT DOCUMENTS

| | | | | |
|---|---|---|---|---|
| 2009/0133260 | A1* | 5/2009 | Durbin | A61C 13/082 29/896.11 |
| 2011/0196654 | A1* | 8/2011 | Genest | A61C 13/0004 703/1 |
| 2012/0015328 | A1* | 1/2012 | Giasson | A61C 13/0004 433/213 |
| 2012/0022834 | A1* | 1/2012 | Lajoie-Dorval | G16H 50/50 703/1 |
| 2012/0070803 | A1* | 3/2012 | Manai | A61C 13/0004 433/213 |
| 2012/0095732 | A1 | 4/2012 | Fisker et al. | |
| 2012/0189182 | A1* | 7/2012 | Liang | A61C 19/00 382/128 |
| 2017/0046486 | A1* | 2/2017 | Cunningham | G06F 3/0482 |

FOREIGN PATENT DOCUMENTS

| | | |
|---|---|---|
| KR | 101854732 B1 | 5/2018 |
| KR | 101862752 B1 | 5/2018 |
| KR | 10-2018-0096138 A | 8/2018 |
| KR | 101875755 B1 | 8/2018 |

OTHER PUBLICATIONS

Nicola U. Zitzmann, Gabriel Krastl, Hanjo Hecker, Clemens Walter, Tuomas Waltimo, Roland Weiger, Strategic considerations in treatment planning: Deciding when to treat, extract, or replace a questionable tooth, The Journal of Prosthetic Dentistry, (Year: 2010).*
International Search Report corresponding to International Application No. PCT/KR2020/002118, dated May 26, 2020. (English translation).
Renishaw Dental Studio Release Notes, Part No. H-5489-4040-05-A, Jun. 2016 (20 pages).
Zfx CAD/Scanner Software User Manual (68 pages).
Supplementary European Search Report corresponding to Patent Application No. EP 20760047.9 dated Sep. 16, 2022 (6 pages).

* cited by examiner

DENTAL FORMULA INFORMATION INPUT METHOD, DENTAL FORMULA INFORMATION INPUT DEVICE, AND RECORDING MEDIUM

CROSS-REFERENCE TO RELATED APPLICATIONS

This application is a U.S. national phase application pursuant to 35 U.S.C. § 371 of PCT/KR2020/002118, filed Feb. 14, 2020, designating the United States, which claims the benefit of and priority to Korean Application No. 10-2019-0019761, filed Feb. 20, 2019. The entire contents of the aforementioned patent applications are incorporated herein by this reference.

TECHNICAL FIELD

The following description relates to a dental formula information input method and device for automatically inputting dental formula information of a tooth in consideration of a prosthetic type, and more specifically, to a technique for improving the usability of a user by pre-storing dental formula information of teeth that is commonly used to perform a prosthetic work on the user according to a prosthetic type.

BACKGROUND ART

Patient information for scanning or CAD work includes additional attributes such as tooth types and tooth numbers. This process is called ① tooth type selection ② tooth number selection ③ tooth detailed attribute selection. The above process is a task that most programs should perform, and the corresponding settings are made individually according to a tooth number.

However, assuming workers process up to 100 cases per day, such operations require performing repetitive input works at least 300 times.

In addition, this had to be repeatedly performed for every case in the conventional patient information input programs. For example, software that runs on a tablet with a small screen has a more complex operation of selection in many cases due to the limited screen size. A method of increasing the usability for a user by performing this input process more efficiently is proposed.

DISCLOSURE OF INVENTION

Technical Goals

An aspect provides a dental formula information input method and device that inputs dental formula information of a plurality of users by storing dental formula information of teeth commonly used according to prosthetic types in a library and inputting dental formula information that is individually input, at once according to a tooth number.

An aspect provides a dental formula information input method and device that minimizes a work of utilizing a dental formula information input function by automatically determining at least one tooth adjacent to a tooth selected by a user according to a prosthetic type.

Technical Solutions

According to an aspect, there is provided a method of inputting dental formula information, the method including selecting a prosthetic type of a tooth using a library, determining at least one tooth number displayed on an oral image for a prosthetic work corresponding to the prosthetic type of the tooth, and inputting dental formula information according to the prosthetic type of the tooth corresponding to the at least one tooth number.

The determining may include determining a tooth number of a tooth selected by a user according to the prosthetic type of the tooth.

The determining may include determining tooth numbers corresponding to a tooth selected by a user according to the prosthetic type of the tooth and a tooth symmetrical to the selected tooth.

The determining may include determining at least one tooth number corresponding to a tooth selected by a user according to the prosthetic type of the tooth and a tooth adjacent to the selected tooth in a leftward or rightward direction.

The determining may include determining a tooth number corresponding to at least one of a crown, a bridge, and an antagonistic tooth according to a prosthetic work type based on tooth numbers, if the prosthetic type of the tooth is not selected.

The dental formula information may include at least one of 1) a tooth manufacturing method, 2) a tooth surface material, and 3) a tooth shade according to the prosthetic type of the tooth.

According to an aspect, there is provided a device for inputting dental formula information, the device including a processor, wherein the processor may be configured to select a prosthetic type of a tooth using a library, determine at least one tooth number displayed on an oral image for a prosthetic work corresponding to the prosthetic type of the tooth, and input dental formula information according to the prosthetic type of the tooth corresponding to the at least one tooth number.

The processor may be configured to determine a tooth number of a tooth selected by a user according to the prosthetic type of the tooth.

The processor may be configured to determine tooth numbers corresponding to a tooth selected by a user according to the prosthetic type of the tooth and a tooth symmetrical to the selected tooth.

The processor may be configured to determine at least one tooth number corresponding to a tooth selected by a user according to the prosthetic type of the tooth and a tooth adjacent to the selected tooth in a leftward or rightward direction.

The processor may be configured to determine a tooth number corresponding to at least one of a crown, a bridge, and an antagonistic tooth according to a prosthetic work type based on tooth numbers, if the prosthetic type of the tooth is not selected.

The dental formula information may include at least one of 1) a tooth manufacturing method, 2) a tooth surface material, and 3) a tooth shade according to the prosthetic type of the tooth.

Effects

According to example embodiments, by automatically inputting dental formula information of teeth according to selection by a dental technician, it is possible to minimize an input operation that is continuously and repeatedly performed for inputting cases associated with prosthetic works such as crowns and bridges for a plurality of users.

According to example embodiments, by automatically inputting dental formula information of a tooth through one click of a prosthetic type on the screen of a user terminal with a different input environment, it is possible to reduce work operations and improve the convenience and usability for a user who repeatedly inputs cases associated with prosthetic works.

According to example embodiments, by inputting dental formula information corresponding to prosthetic types through one click, it is possible to minimize input errors made by a dental technician and increase the quality of dental formula information.

BEST MODE FOR CARRYING OUT THE INVENTION

Hereinafter, example embodiments will be described in detail with reference to the accompanying drawings. However, various alterations and modifications may be made to the example embodiments. Here, the example embodiments are not construed as limited to the disclosure. The example embodiments should be understood to include all changes, equivalents, and replacements within the idea and the technical scope of the disclosure.

The terminology used herein is for the purpose of describing particular example embodiments only and is not to be limiting of the example embodiments. The singular forms "a", "an", and "the" are intended to include the plural forms as well, unless the context clearly indicates otherwise. It will be further understood that the terms "comprises/comprising" and/or "includes/including" when used herein, specify the presence of stated features, integers, steps, operations, elements, and/or components, but do not preclude the presence or addition of one or more other features, integers, steps, operations, elements, components and/or groups thereof.

Unless otherwise defined, all terms including technical and scientific terms used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein.

When describing the example embodiments with reference to the accompanying drawings, like reference numerals refer to like constituent elements and a repeated description related thereto will be omitted. In the description of example embodiments, detailed description of well-known related structures or functions will be omitted when it is deemed that such description will cause ambiguous interpretation of the present disclosure.

Figure 1:
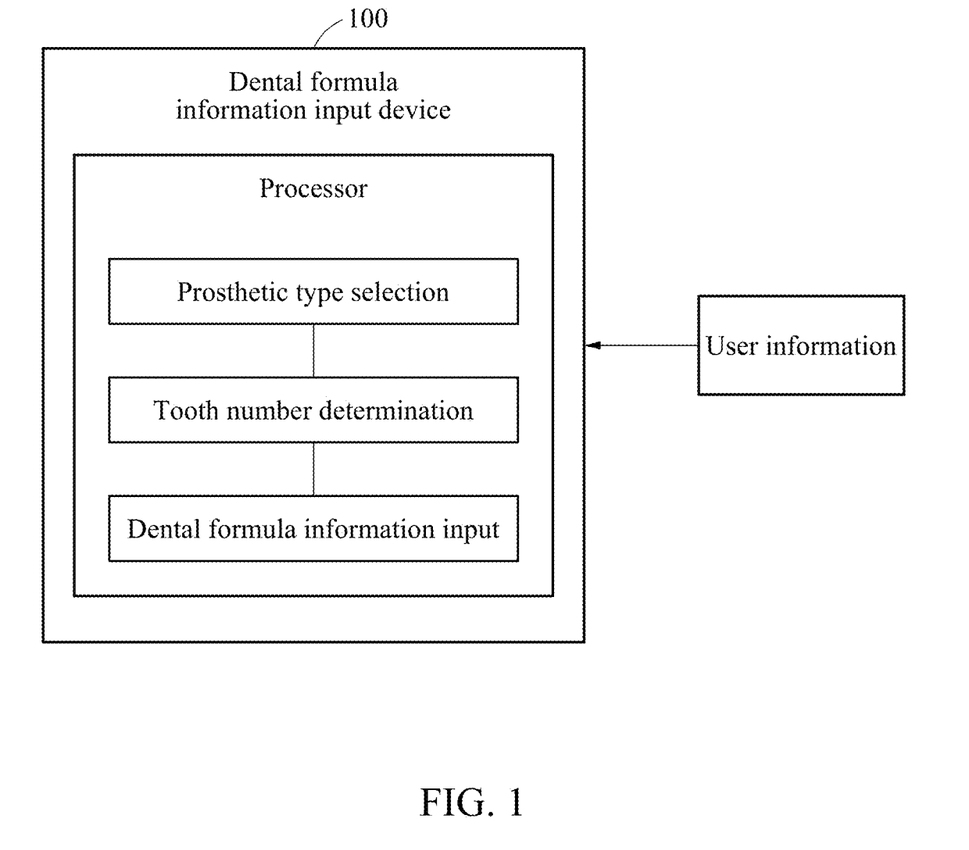
FIG. 1 illustrates a dental formula information input device according to an example embodiment.

FIG. 1 illustrates a dental formula information input device according to an example embodiment.

Referring to FIG. 1, a dental formula information input device 100 may automatically input dental formula information of a user for dental treatment. To this end, the dental formula information input device 100 may include a processor. The processor may automatically input dental formula information corresponding to a tooth number according to a prosthetic type based on a library.

To this end, the dental formula information input device 100 may store dental formula information of teeth that is commonly used according to prosthetic types in the library. Here, the library may be a data storage for storing dental formula information of teeth that is commonly used for prosthetic works.

Here, data storable in the library may include at least one of 1) a tooth manufacturing method, 2) a tooth surface material, and 3) a tooth shade corresponding to a prosthetic type of a tooth. Such data may be information that is commonly used in dental clinics to perform a prosthetic work on a user. In addition, the data storable in the library may be added or changed according to the dental condition of the user or as needed by a dental technician.

The dental formula information input device 100 may collectively perform operations of inputting dental formula information that is individually performed for a plurality of users, through the following process.

The dental formula information input device 100 may receive information of users whose dental formula information of teeth is to be input. The information of users may include basic information to identify individuals, such as names, genders, and the like, oral images such as panoramic images, and the like.

The dental formula information input device 100 may receive, from the user, a selection of a prosthetic type of a tooth for a prosthetic work according to the dental condition of the user based on the library. In more detail, when a tooth is damaged and broken or badly decayed, the user may receive dental treatment for completely encircling the tooth after treatment. Dental treatments may largely include:

ceramic, which is often used for front teeth as visually similar to natural teeth, has high biocompatibility, and causes no allergic reaction;

zirconia, which has very high hardness, colors most similar to those of natural teeth, and an excellent aesthetic impression, and provides great wearing sensation and less foreign body sensation; and PFM, which includes a metallic inside that has high hardness and a ceramic surface that is hard to notice. However, the metallic inside may be seen through over time.

The dental formula information input device 100 may determine at least one tooth number displayed in an oral image for a prosthetic work corresponding to the prosthetic type of the tooth. In detail, a dental technician who inputs dental formula information of users may perform a series of operations to input dental formula information of a user. In other words, the dental technician may input a prosthetic type, a tooth number, and dental formula information of the user to perform a prosthetic work. The above operations may be performed through a user interface in the dental formula information input device 100. Dental formula information input through the user interface merely differs only in dental numbers according to prosthetic types, but similar settings may be used in many cases.

The dental formula information input device 100 may select a tooth number for automatically inputting dental formula information corresponding to the prosthetic type of the user. To this end, the dental technician may perform a mouse hover (mouse rollover) over the oral image with tooth numbers displayed. Also, the dental formula information input device 100 may determine at least one tooth number selected by the dental technician by identifying coordinates of the mouse hover on the user interface.

The dental formula information input device 100 may input dental formula information according to the prosthetic type of the tooth corresponding to the at least one tooth number.

As a result, the dental formula information input device 100 may provide the user interface for automatically inputting dental formula information of users, thereby minimizing an input operation that is repeatedly performed for every case according to a dental condition of a user.

Further, the dental formula information input device 100 may automatically input dental formula information of a tooth through one click of a prosthetic type on the screen of a user terminal with a different input environment, thereby reducing the work operations and improving the convenience and usability for a user who repeatedly inputs cases associated with prosthetic works.

Figure 2:
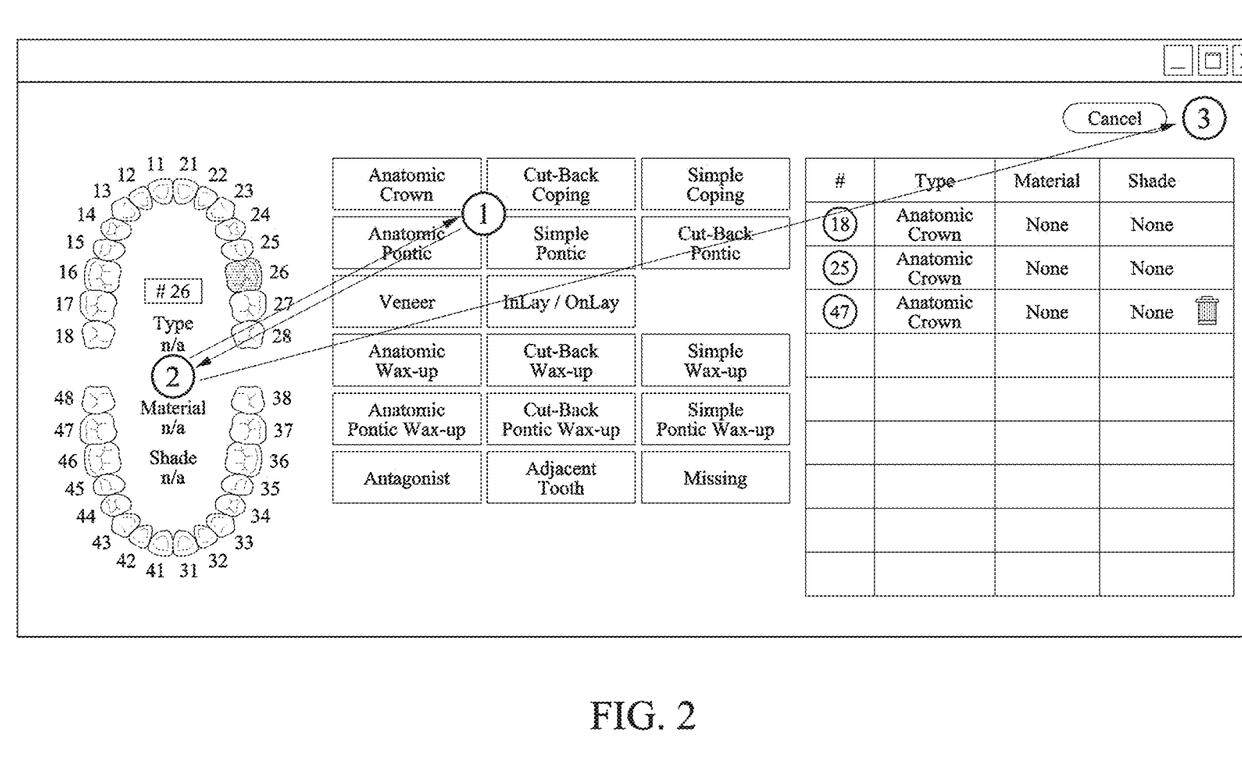
FIG. 2 illustrates a detailed interface of a dental formula information input device according to an example embodiment.

FIG. 2 illustrates a detailed user interface of a dental formula information input device according to an example embodiment.

Referring to FIG. 2, a dental formula information input device may display a user interface for automatically inputting dental formula information of teeth. The dental formula information input device may display an oral image included in user information on a screen. Tooth numbers of the teeth may be displayed in the oral image. Since it is difficult to communicate as teeth have long unique names, the tooth numbers may substitute for the names to indicate the positional relationship. The tooth numbers may be expressed by numbers 11 to 18 for upper right teeth, 21 to 28 for upper left teeth, 31 to 38 for lower left teeth, and 41 to 48 for upper right teeth, based on the midline and the occlusal surface.

The dental formula information input device may display a prosthetic type of a tooth selected by the dental technician in interoperation with a library. Dental prosthetic types may be shown in Table 1 below, and include various types according to dental treatment manners.

TABLE 1

| | | |
|---|---|---|
| Anatomic Crown | Cut-Back Coping | Simple Coping |
| Anatomic Pontic | Simple Pontic | Cut-Back Pontic |
| Veneer | Inlay/Onlay | |
| Anatomic Wax-up | Cut-Back Wax-up | Simple Wax-up |
| Anatomic Pontic Wax-up | Cut-Back Pontic Wax-up | Simple Pontic Wax-up |
| Antagonist | Adjacent Tooth | Missing |

Further, the prosthetic types of teeth may be defined as any types that are used frequently by the dental technician. The prosthetic types of teeth may be added or changed according to the dental condition of the user or as needed by the dental technician.

When a tooth number corresponding to the prosthetic type of the tooth is selected, the dental formula information input device may automatically input dental formula information according to the prosthetic type of the tooth. For example, "Anatomic Crown" may be selected as the prosthetic type of the tooth, and at least one tooth number may be selected through a hover by the dental technician. In this case, a tooth number corresponding to a tooth to be treated with an anatomic crown may be selected.

The dental formula information input device may automatically select "Milling R40" as a tooth manufacturing method, "Composite" as a tooth surface material, and "A2" as a tooth shade, corresponding to "Anatomic Crown" and the selected at least one tooth number. Teeth may be represented in various shades according to an oral environment of an individual.

In more detail, tooth shades for most users in dentistry may be similar. Almost similar shades may be frequently used for anterior/posterior teeth of the users. In addition, similar tooth types such as an anatomic crown and an inlay may be used as the prosthetic types of teeth. The users may merely have different tooth numbers (positions), but in many cases, similar dental formula information settings may be used.

Further, the conventional dental formula information input devices had to repeatedly perform this for every case. For example, software that runs on a tablet with a small screen has a more complex operation of selection in many cases due to the limited screen size.

Accordingly, the dental formula information input device proposed herein may perform a method for increasing the usability for a user by performing this input process more efficiently. That is, the dental formula information input device may automatically input dental formula information of a desired teeth by storing frequent cases in the library.

Furthermore, the dental formula information input device may automatically input dental formula information in relation to a more fundamental input operation. For example, the dental formula information input device may utilize, as a method for automatically generating dental formula information of teeth, an automatic dental formula information input function based on data received through our own patient information input programs such as OneClick and PMS, thereby minimizing the input operation of the dental technician.

Figure 3:
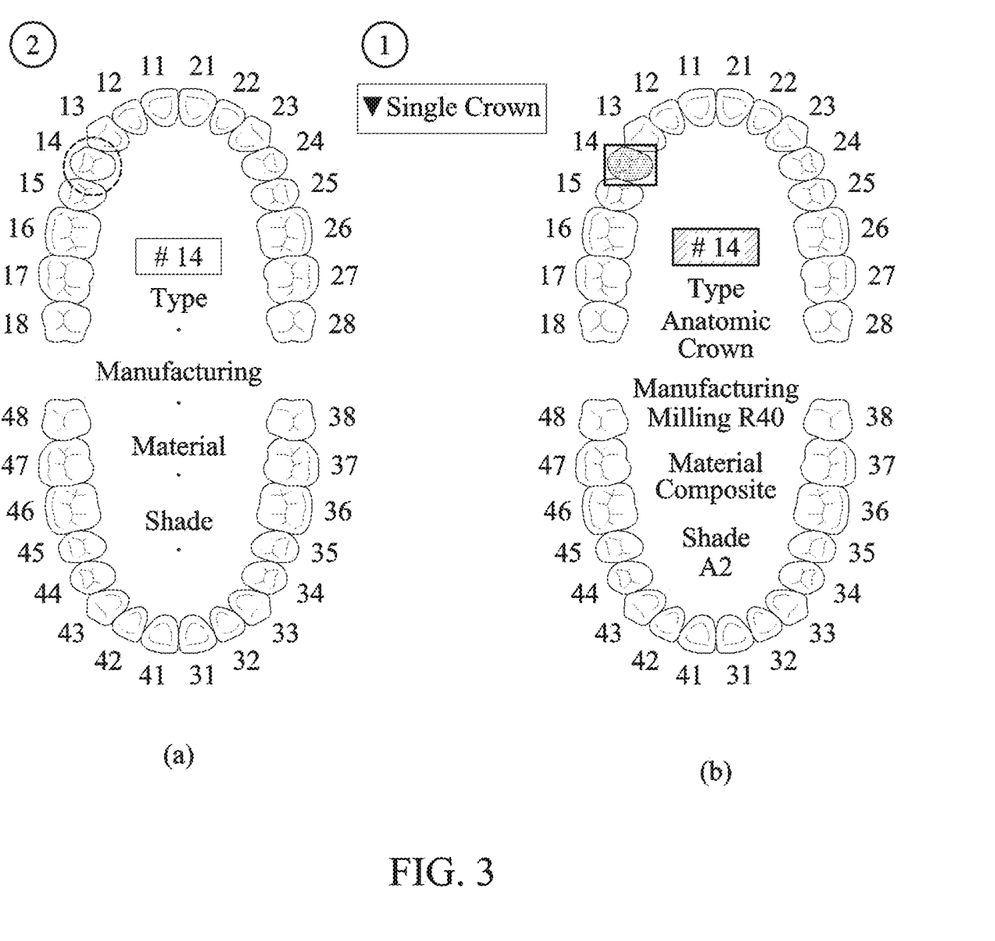
FIG. 3 illustrates an operation of automatically inputting dental formula information of a tooth according to an example embodiment.

FIG. 3 illustrates an operation of automatically inputting dental formula information of a tooth according to an example embodiment.

Referring to FIG. 3, a dental formula information input device may select a prosthetic type of a tooth using a library. In addition, the dental formula information input device may determine at least one tooth number displayed in an oral image for a prosthetic work and then, automatically input dental formula information according to a prosthetic type of a tooth corresponding to the at least one tooth number.

Referring to (a) of FIG. 3, the dental formula information input device may select a prosthetic type of a tooth using the library. The dental formula information input device may select a prosthetic type related to "Single Crown" from among a plurality of dental prosthetic types included in the library. For example, the dental formula information input device may select a single library as the prosthetic type related to "Single Crown".

The dental formula information input device may determine at least one tooth number displayed in an oral image for a prosthetic work corresponding to the prosthetic type of the tooth. In more detail, a dental technician may perform a mouse hover (mouse rollover) over a tooth to be selected in the oral image.

Referring to (b) of FIG. 3, the dental formula information input device may activate the edge of the tooth selected by the hover in the oral image, change the color of the tooth, and determine. The dental formula information input device may determine a tooth number of the tooth selected by the user according to the prosthetic type of the tooth. For example, the dental formula information input device may display a tooth in color to indicate that the tooth is provisionally selected, when the tooth is selected (the mouse hover is performed over the tooth to be selected). This may help the dental technician to recognize that the desired tooth is selected.

The dental formula information input device may automatically input dental formula information according to the prosthetic type of the tooth corresponding to the at least one tooth number. The dental formula information input device may automatically input 1) a tooth manufacturing method, 2) a tooth surface material, and 3) a tooth shade according to the prosthetic type of the tooth.

The dental formula information input device may minimize the repetitive works for information that should be input. In addition, if a small monitor such as a tablet PC is used, the dental formula information input device provided herein may reduce the operations for the input operation, thereby improving the usability and utilization for the dental technician. The dental formula information input device may efficiently input dental input information by increasing the usability and utilization for the dental technician.

Figure 4:
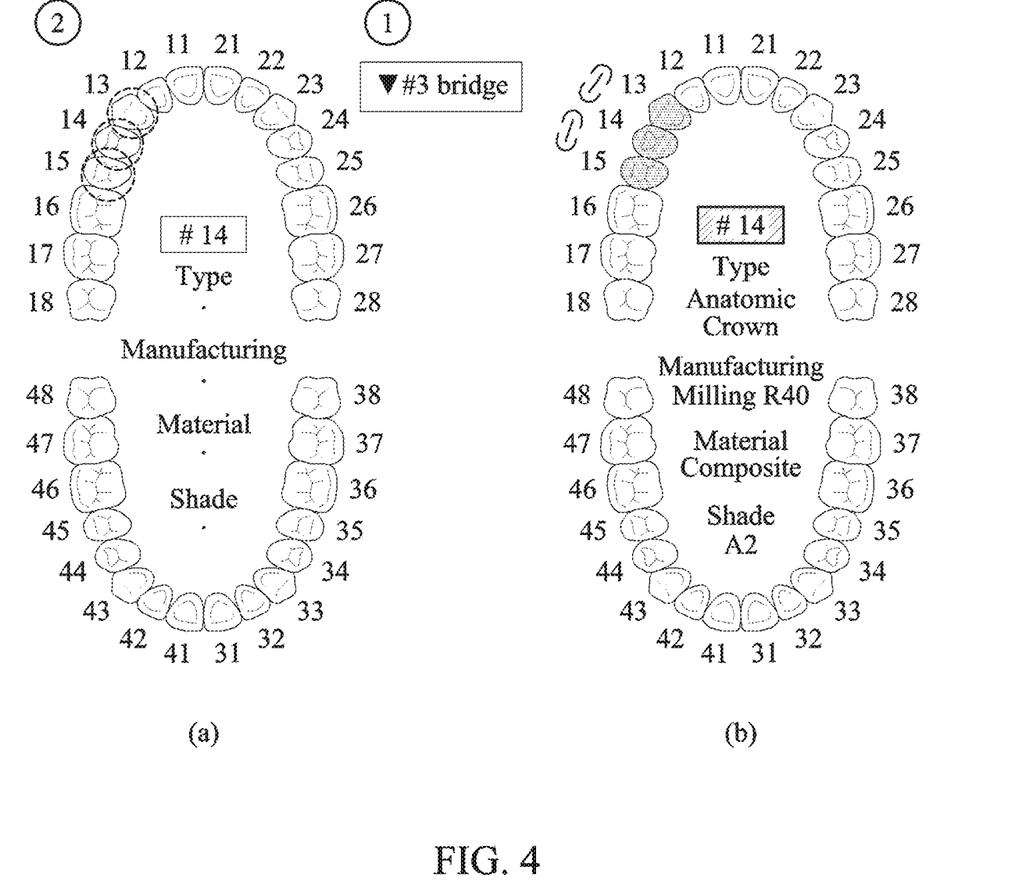
FIG. 4 illustrates an operation of automatically inputting dental formula information of a tooth according to another example embodiment.

FIG. 4 illustrates an operation of automatically inputting dental formula information of a tooth according to another example embodiment.

Referring to FIG. 4, a dental formula information input device may select a prosthetic type of a tooth using a library. In addition, the dental formula information input device may determine at least one tooth number displayed in an oral image for a prosthetic work and then, automatically input dental formula information according to a prosthetic type of a tooth corresponding to the at least one tooth number.

Referring to (a) of FIG. 4, the dental formula information input device may select a prosthetic type of a tooth using the library. The dental formula information input device may select a prosthetic type related to "#3 bridge" from among a plurality of dental prosthetic types included in the library. For example, the dental formula information input device may select a bridge library as the prosthetic type related to "Single Crown".

The dental formula information input device may determine at least one tooth number displayed in an oral image for a prosthetic work corresponding to the prosthetic type of the tooth. In more detail, a dental technician may perform a mouse hover (mouse rollover) over a tooth to be selected in the oral image.

Referring to (b) of FIG. 4, the dental formula information input device may activate the edge of the tooth selected by the hover in the oral image, change the color of the tooth, and determine. In this case, the dental information input device may determine tooth numbers of adjacent or symmetrical teeth according to the coordinates of the mouse hovered on the user interface in consideration of the prosthetic type of the tooth.

In other words, the dental formula information input device may determine tooth numbers corresponding to a tooth selected by a user according to the prosthetic type of the tooth and a tooth symmetrical to the selected tooth. Further, the dental formula information input device may determine at least one tooth number corresponding to a tooth selected by a user according to the prosthetic type of the tooth and a tooth adjacent to the selected tooth in a leftward or rightward direction.

As an example, when the tooth number of the tooth selected by the mouse hover is an odd number, the dental formula information input device may select a tooth number of a tooth on the left or right side of the selected tooth. As another example, when the tooth number of the tooth selected by the mouse hover is an even number, the dental formula information input device may select a tooth number of a tooth on the right side of the selected tooth.

The dental formula information input device may automatically input dental formula information according to the prosthetic type of the tooth corresponding to the at least one tooth number. The dental formula information input device may automatically input 1) a tooth manufacturing method, 2) a tooth surface material, and 3) a tooth shade according to the prosthetic type of the tooth. The dental formula information input device may apply the same prosthetic information and detailed attribute information to the tooth numbers of the selected teeth.

The dental formula information input device may pre-store commonly used settings for different tooth numbers, thereby improving the usability for the user.

Figure 5:
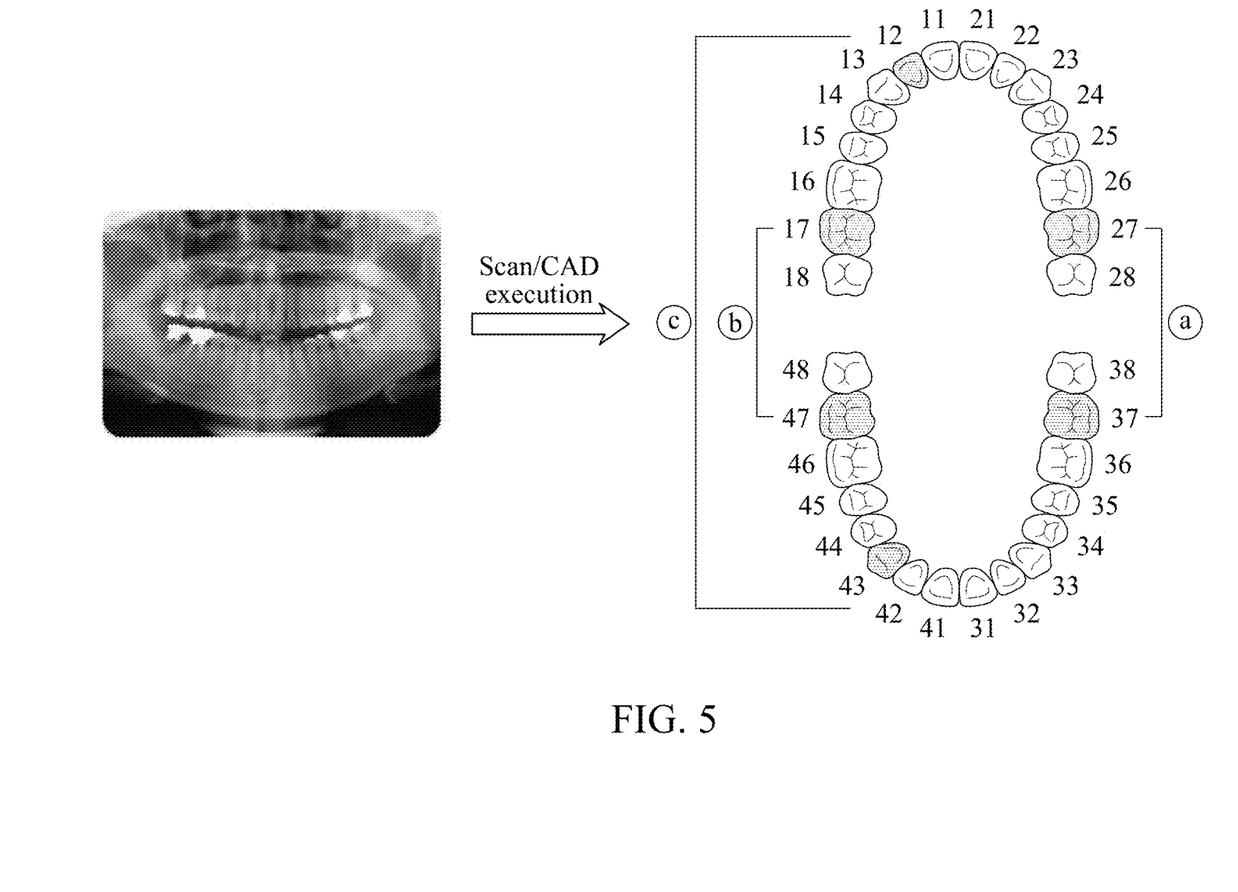
FIG. 5 illustrates an operation of automatically inputting dental formula information of a tooth according to still another example embodiment.

FIG. 5 illustrates an operation of automatically inputting dental formula information of a tooth according to still another example embodiment.

Referring to FIG. 5, the dental formula information input device may experience a case in which a prosthetic type of a tooth is not selected. Accordingly, the dental formula information input device may determine a tooth number corresponding to at least one of a crown, a bridge, and an antagonistic tooth according to a prosthetic work type based on tooth numbers.

In detail, the dental formula information input device may determine a tooth number corresponding to at least one of a crown, a bridge, and an antagonistic tooth, if a prosthetic type of a tooth is not selected through a patent information system. The dental formula information input device may determine the tooth number based on the following basic information. The basic information may include patient basic information (name/gender, etc.), an oral image such as a panoramic image, tooth number information, and a prosthetic type. When there is no prosthetic information, the panoramic image may be used to classify a prosthetic type selected by a dental technician.

The dental formula information input device may automatically input dental formula information of the user based on the basic information.

Figure 6:
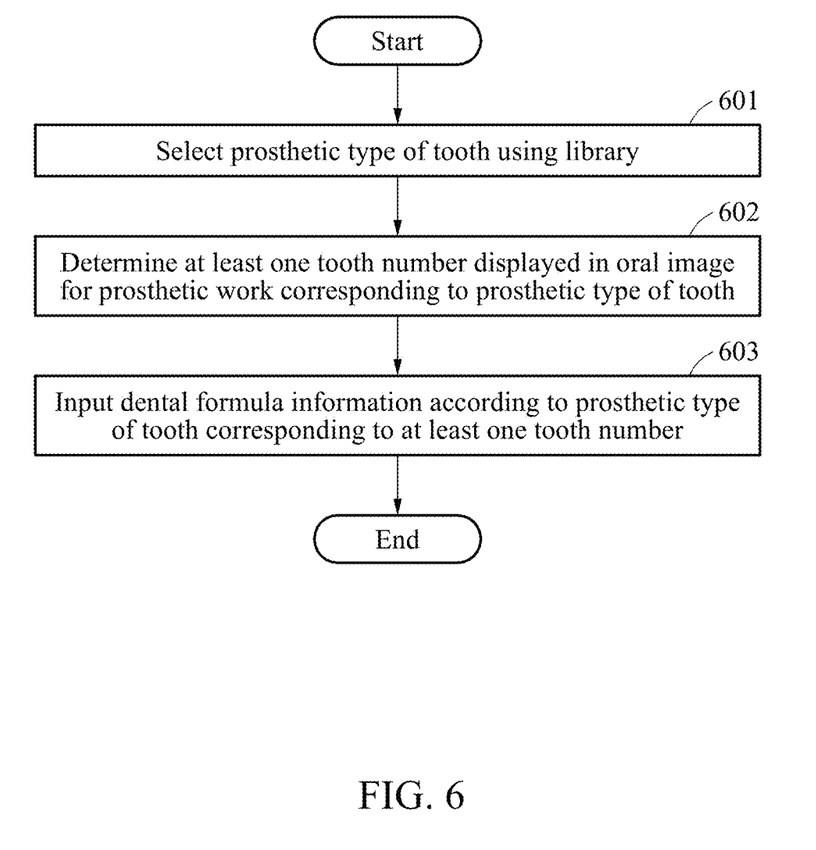
FIG. 6 is a flowchart illustrating a dental formula information input method according to an example embodiment.
Figure 7:
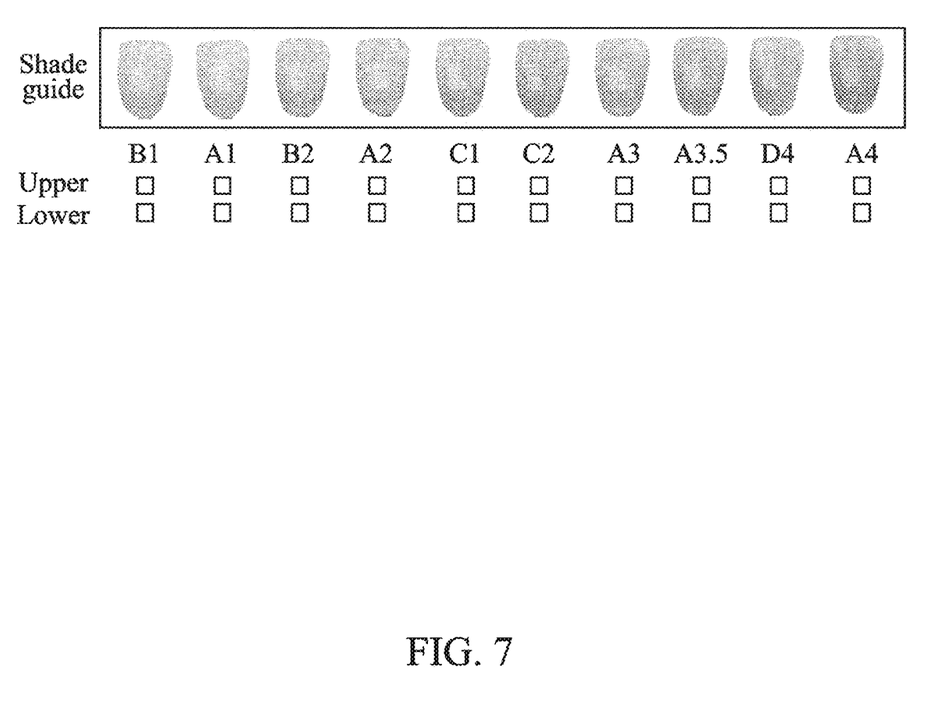
FIG. 7 illustrates tooth shades according to an example embodiment.

FIG. 6 is a flowchart illustrating a dental formula information input method according to an example embodiment.

In operation 601, a dental formula information input device may select a prosthetic type of a tooth using a library. In detail, the dental formula information input device may select the prosthetic type of the tooth for inputting order information of the user from among a plurality of prosthetic types stored in the library.

In operation 602, the dental formula information input device may determine at least one tooth number displayed on an oral image for a prosthetic work corresponding to the prosthetic type of the tooth. The tooth number may be determined according to the following cases.

CASE 1: The dental formula information input device may determine a tooth number of the tooth selected by the user according to the prosthetic type of the tooth.

CASE 2: The dental formula information input device may determine tooth numbers corresponding to a tooth selected by the user according to the prosthetic type of the tooth and a tooth symmetrical to the selected tooth.

CASE 3: The dental formula information input device may determine at least one tooth number corresponding to a tooth selected by the user according to the prosthetic type of the tooth and a tooth adjacent to the selected tooth in a leftward or rightward direction.

CASE 4: The dental formula information input device may determine a tooth number corresponding to at least one of a crown, a bridge, and a dental antagonist according to a prosthetic work type based on tooth numbers, if a prosthetic type of a tooth is not selected.

The tooth number may be determined based on a treatment method by the prosthetic type of the tooth. In other words, the prosthetic type of the tooth may be a prosthetic type for replacing a natural tooth with an artificial tooth to restore a lost tooth. Also, the dental formula information input device may determine at least one tooth number corresponding to a treatment method of a tooth according to the prosthetic type.

In operation 603, the dental formula information input device may input dental formula information according to the prosthetic type of the tooth corresponding to the determined at least one tooth number.

Further, as described above, the dental formula information input device may be applied not only to a scheme of selecting a project for each user but also to a scheme of processing user information of a plurality of users collectively. In other words, the dental formula information input device proposed herein may be provided to alleviate the inconvenience of repeatedly generating a case for each of the plurality of users. In addition, the dental formula information input device may receive user information collectively, group the users according to similarity of works, and generate cases for the groups collectively.

As an example, the dental formula information input device may identify users who want to create crowns and users who want to create bridges according to user information, and then assign respectively a case identification number to the users who want to create crowns, collectively. In addition, the dental formula information input device may select subdivided information (tooth numbers, etc.) for each case after assigning the case identification number.

Also, the dental formula information input device may automatically input dental formula information by using an information matching method between a patient information input program and a case generating program. In other words, the dental formula information input device may preset a conversion relationship for mapping data between the patient information input program and the case generating program (ex. CAD). For example, the dental formula information input device may link user information input through PMS or OneClick with a work or a tooth number determined when generating a case. The dental formula information input device may automatically input dental formula information of the tooth based on the linked information.

In addition, the dental formula information input device may assign case numbers according to work similarity. Since the dental formula information input device is for workers who perform scanning or CAD works multiple times, it may assign case numbers according to work similarity, rather than connecting different works. As an example, the dental formula information input device may set time intervals (ex. 5 days) from a work request date, reassign works according to work similarity, work difficulty level, and user attribute similarity, and assign case numbers based on the reassigned works, thereby processing successive and similar works at once.

In the meantime, the dental formula information input method of automatically inputting dental formula information corresponding to a tooth number selected by a user for a prosthetic work based on a library storing dental formula information of teeth according to prosthetic types according to an example embodiment may be implemented as various recording media such as a magnetic storage medium, an optical read medium, and a digital storage medium after being implemented as a program that can be executed in a computer.

The implementations of the various technologies described in the specification may be implemented with a digital electronic circuit, computer hardware, firmware, software, or the combinations thereof. The implementations may be achieved as a computer program product, for example, a computer program tangibly embodied in a machine readable storage device (a computer-readable medium) to process the operations of a data processing device, for example, a programmable processor, a computer, or a plurality of computers or to control the operations. The computer programs such as the above-described computer program(s) may be recorded in any form of a programming language including compiled or interpreted languages, and may be executed as a standalone program or in any form included as another unit suitable to be used in a module, component, sub routine, or a computing environment. The computer program may be executed to be processed on a single computer or a plurality of computers at one site or to be distributed across a plurality of sites and then interconnected by a communication network.

The processors suitable to process a computer program include, for example, both general purpose and special purpose microprocessors, and any one or more processors of a digital computer of any kind. Generally, the processor may receive instructions and data from a read only memory, a random access memory or both of a read only memory and a random access memory. The elements of a computer may include at least one processor executing instructions and one or more memory devices storing instructions and data. In general, a computer may include one or more mass storage devices storing data, such as a magnetic disk, a magneto-optical disc, or an optical disc or may be coupled with them so as to receive data from them, to transmit data to them, or to exchange data with them. For example, information carriers suitable to embody computer program instructions and data include semiconductor memory devices, for example, magnetic Media such as hard disks, floppy disks, and magnetic tapes, optical Media such as compact disc read only memory (CD-ROM), and digital video disc (DVD), magneto-optical media such as floppy disks, ROM, random access memory (RAM), flash memory, erasable programmable ROM (EPROM), electrically erasable programmable ROM (EEPROM), and the like. The processor and the memory may be supplemented by a special purpose logic circuit or may be included by the special purpose logic circuit.

Furthermore, the computer-readable medium may be any available medium capable of being accessed by a computer and may include a computer storage medium.

Although the specification includes the details of a plurality of specific implementations, it should not be understood that they are restricted with respect to the scope of any invention or claimable matter. On the contrary, they should be understood as the description about features that may be specific to the specific example embodiment of a specific invention. Specific features that are described in this specification in the context of respective embodiments may be implemented by being combined in a single embodiment. On the other hand, the various features described in the context of the single embodiment may also be implemented in a plurality of embodiments, individually or in any suitable sub-combination. Furthermore, the features operate in a specific combination and may be described as being claimed. However, one or more features from the claimed combination may be excluded from the combination in some cases. The claimed combination may be changed to sub-combinations or the modifications of sub-combinations.

Likewise, the operations in the drawings are described in a specific order. However, it should not be understood that such operations need to be performed in the specific order or sequential order illustrated to obtain desirable results or that all illustrated operations need to be performed. In specific cases, multitasking and parallel processing may be advantageous. Moreover, the separation of the various device components of the above-described embodiments should not be understood as requiring such the separation in all embodiments, and it should be understood that the described program components and devices may generally be integrated together into a single software product or may be packaged into multiple software products.

In the meantime, embodiments of the present invention disclosed in the specification and drawings are simply the presented specific example to help understand an embodiment of the present invention and not intended to limit the scopes of embodiments of the present invention. It is obvious to those skilled in the art that other modifications based on the technical idea of the present invention may be performed in addition to the embodiments disclosed herein.

The invention claimed is:

1. A method of inputting dental formula information performed by a device for inputting the dental information by using a user interface displayed on a monitor, the method comprising:
    displaying the user interface including an oral image of a patient generated from a panoramic image on the monitor;
    selecting a prosthetic type of a tooth for a prosthetic work from among a plurality of prosthetic types from a library;
    receiving a hovering over a tooth in the oral image for which the prosthetic work is required through the user interface;
    activating an edge of the tooth hovered over in the oral image and activating an edge of one or more teeth adjacent to the tooth hovered over or a tooth symmetrical to the tooth hovered over in the oral image;
    changing a color of the tooth hovered over in the oral image and changing a color of the one or more teeth adjacent to the tooth hovered over or the tooth symmetrical to the tooth hovered over, wherein the prosthetic type of the tooth will be applied to teeth that color changed;
    determining a tooth number corresponding to the tooth hovered over based on hovered coordinates and determining a tooth number corresponding to the one or more teeth adjacent to the tooth hovered over or a tooth symmetrical to the tooth hovered over;
    inputting the dental formula information according to the prosthetic type to the tooth hovered over and inputting the dental formula information to the one or more teeth adjacent to the tooth hovered over or the tooth symmetrical to the tooth hovered over; and
    displaying the oral image, the oral image including the tooth or teeth with changed color together with the dental formula information, on the monitor through the user interface;
    wherein the dental formula information displayed on the monitor through the user interface is matched and stored with the prosthetic type of the tooth selected from the library as one case.

2. The method of claim 1, wherein the determining comprises determining the tooth number of the tooth hovered over further based on the prosthetic type of the tooth.

3. The method of claim 1, wherein the dental formula information comprises at least one of 1) a tooth manufacturing method, 2) a tooth surface material, and 3) a tooth shade according to the prosthetic type of the tooth,
    wherein at least one of 1) the tooth manufacturing method, 2) the tooth surface material, and 3) the tooth shade is matched with the prosthetic type of the tooth,
    wherein at least one of 1) the tooth manufacturing method, 2) the tooth surface material, and 3) the tooth shade is stored in the library as one case with the matched prosthetic type of the tooth, and
    wherein the inputting comprises inputting at least one of 1) the tooth manufacturing method, 2) The tooth surface material, and 3) the tooth shade matched with the prosthetic type of the tooth in the one case as the dental formula information.

4. The method of claim 1, further including providing the patient with a treatment that includes the prosthetic work.

5. The method of claim 1, wherein the selecting the prosthetic type is based on a dental condition of the patient.

6. A non-transitory computer-readable storage medium storing instructions that, when executed by a processor, cause the processor to perform the method of claim 1.

7. A device for inputting dental formula information, the device including a user interface displayed on a monitor, the device comprising:
    a processor,
    wherein the processor is configured to:
    display the user interface including an oral image of a patient generated from a panoramic image on the monitor,
    select a prosthetic type of a tooth for a prosthetic work from among a plurality of prosthetic types from in a library,
    receive a hovering over a tooth in the oral image for which the prosthetic work is required through the user interface,
    activate an edge of the tooth hovered over in the oral image and activate an edge of one or more teeth adjacent to the tooth hovered over or a tooth symmetrical to the tooth hovered over in the oral image,
    change a color of the tooth hovered over in the oral image and change a color of the one or more teeth adjacent to the tooth hovered over or the tooth symmetrical to the tooth hovered over, wherein the prosthetic type of the tooth will be applied to teeth with changed color,
    determine a tooth number corresponding to the tooth hovered over based on hovered coordinates and determine a tooth number corresponding to the one or more teeth adjacent to the tooth hovered over or a tooth symmetrical to the tooth hovered over,
    input the dental formula information according to the prosthetic type to the tooth hovered over and input the dental formula information to the one or more teeth adjacent to the tooth hovered over or the tooth symmetrical to the tooth hovered over; and display the oral image, the oral image including the tooth or teeth with changed color together with the dental formula information on the monitor through the user interface;

wherein the dental formula information displayed on the monitor through the user interface is matched and stored with the prosthetic type of the tooth selected from the library as one case.

8. The device of claim 7, wherein the processor is configured to determine the tooth number of the tooth hovered over by the user according to the prosthetic type of the tooth.

9. The device of claim 7, wherein the dental formula information comprises at least one of 1) a tooth manufacturing method, 2) a tooth surface material, and 3) a tooth shade according to the prosthetic type of the tooth, wherein at least one of 1) the tooth manufacturing method, 2) the tooth surface material, and 3) the tooth shade is matched with the prosthetic type of the tooth, wherein at least one of 1) the tooth manufacturing method, 2) the tooth surface material, and 3) the tooth shade is stored in the library as one case with the matched prosthetic type of the tooth, and wherein the processor is configured to input at least one of 1) the tooth manufacturing method, 2) the tooth surface material, and 3) the tooth shade matched with the prosthetic type of the tooth in the one case as the dental formula information.

\* \* \* \* \*